United States Patent [19]

Liburdy

[11] 4,238,327
[45] Dec. 9, 1980

[54] ELECTRIC RESONANCE CHROMATOGRAPHY

[76] Inventor: Robert P. Liburdy, 54 Pomeroy Ave., Pittsfield, Mass. 01201

[21] Appl. No.: 52,177

[22] Filed: Jun. 25, 1979

[51] Int. Cl.³ ............................................. B01D 15/08
[52] U.S. Cl. .................................. 210/656; 210/198.2
[58] Field of Search .................. 210/31 C, 198; 55/67, 55/386

[56] References Cited

U.S. PATENT DOCUMENTS

| | | | |
|---|---|---|---|
| 3,341,732 | 9/1967 | Malvin et al. ...................... | 55/386 X |
| 3,782,078 | 1/1974 | Jerpe ................................. | 210/198 C |

FOREIGN PATENT DOCUMENTS 50-152194 12/1975 Japan ...................................... 210/31 C Primary Examiner—John Adee Attorney, Agent, or Firm—Joseph E. Rusz; Casimer K. Salys

[57] ABSTRACT

A process and apparatus for enhancing the separation of molecules, such as cells or proteins, into distinct populations based on their interactions with an externally imposed varying electric field during liquid gel chromatography (LGC). An electric field, at radio frequency (RF), is created between two plates of a capacitor structure and impressed through the gel media column situated between the plates. The varying field interacts with the molecules through polarization events that alter the molecular vibration and rotation motions. The induced changes cause the molecules to exhibit elution characteristics distinct from those normally obtained during LGC. Thereby, molecules can be further and more selectively partitioned according to their distinct polarization properties.

8 Claims, 9 Drawing Figures

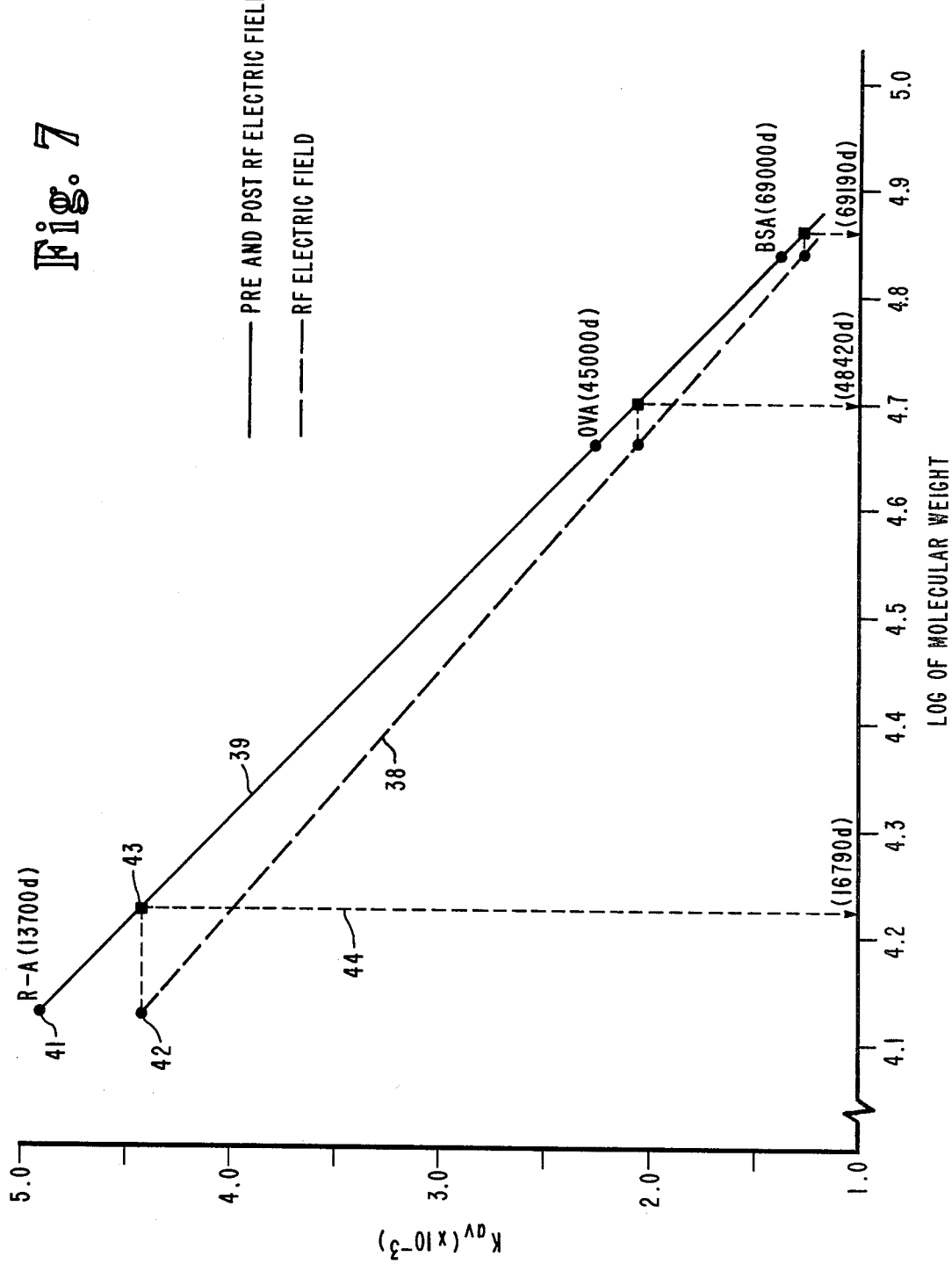

ELECTRIC RESONANCE CHROMATOGRAPHY

RIGHTS OF THE GOVERNMENT

The invention described herein may be manufactured and used by or for the Government of the United States for all governmental purposes without the payment of any royalty.

BRIEF SUMMARY

The invention disclosed herein pertains to processes and apparatus for performing electric resonance chromatography (ERC). Mixtures of molecules passing through a liquid gel chromatography (LGC) column are simultaneously subjected to a varying frequency electric field. Resonance and dipole movement effects in the molecules shift, narrow and otherwise improve the distinctive character of the detected elution patterns attributable to the individual molecules in the sample population.

The electric field to which the molecules are subjected is of a high intensity, and is impressed in a direction substantially transverse to the LGC column and molecular flowing therethrough. In one form, the varying frequency of this field is selected to oscillate near the resonant frequencies of the molecules and the dipoles within their structural chain. The net and individual dipoles of the molecules are stimulated into new vibration and rotation modes, causing the molecules undergoing ERC to exhibit new and unique elution patterns, such as ones in which the apparent molecular weight and strokes radius have increased.

Partitioning by gel permeation type ERC generates separation patterns which are characterized by early elution and reduced zone broadening. Furthermore, since the observed effect on the partition coefficient appears to differ among various cell and protein molecules subjected to ERC, these distinguishing characteristics improve the identification of the various molecules comprising the population.

DESCRIPTION OF THE DRAWINGS

FIG. 7 contains plots of partition coefficient $K_{av}$, and shows the effects of the electric field in terms of apparent molecular weight.

DETAILED DESCRIPTION

Figure 1A:
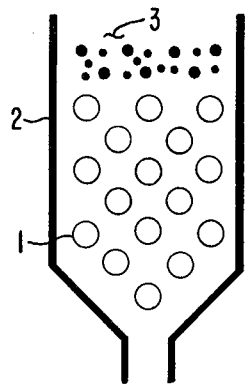
FIGS. 1a, 1b and 1c schematically show three stages of simple gel permeation type liquid gel chromatography (LGC).
Figure 1B:
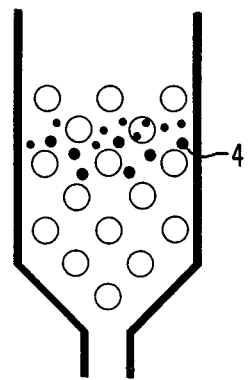
Figure 1C:
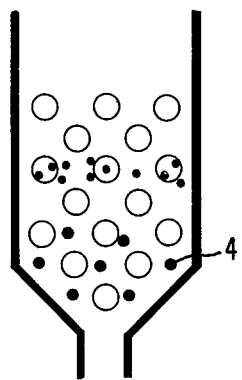

Liquid gel chromatography (LGC) is an established laboratory technique for fractionation and separation of molecules according to weight. The underlying premise for the technique is that molecules elute from the gel bed in order of decreasing molecular weight. This may be shown by utilizing FIGS. 1a, 1b and 1c, in which the three stages of simple gel permeation partitioning in a descending column are schematically illustrated. Gel particles 1 fill column 2 to form a bed. When the molecules to be partitioned, 3, such as cells or proteins, are introduced and driven through the bed by a supplemental eluent, the molecules separate on the basis of molecular weight. The larger molecules, 4, separate and elute first. Thus, the elution order is one of descending size. Since LGC in general, and gel permeation type LGC in particular, are well known by those practicing in the related arts, and are adequately described in references such as U.S. Pat. No. 3,002,823 to P. G. M. Flodin et al, further elaboration is superfluous.

Though a multitude of refinements have been developed to improve the distinctness of the partitioning and increase its rate, better resolution of molecular species on the basis of weight and shape continues to be sought. This is particularly true when complex cell or protein populations, such as biological fluids, are being separated. In such cases, the conventional approaches involve successive LGC filtration steps or the concurrent use of other separation methods in conjunction with LGC.

Electric resonance chromatography (ERC) alters conventional LGC techniques to both accelerate separation and accentuate the ability to distinctly identify molecular groups within the population undergoing analysis. In gel filtration terms, the elution time is decreased while the zones representing particular molecular groups are narrowed.

Figure 2:
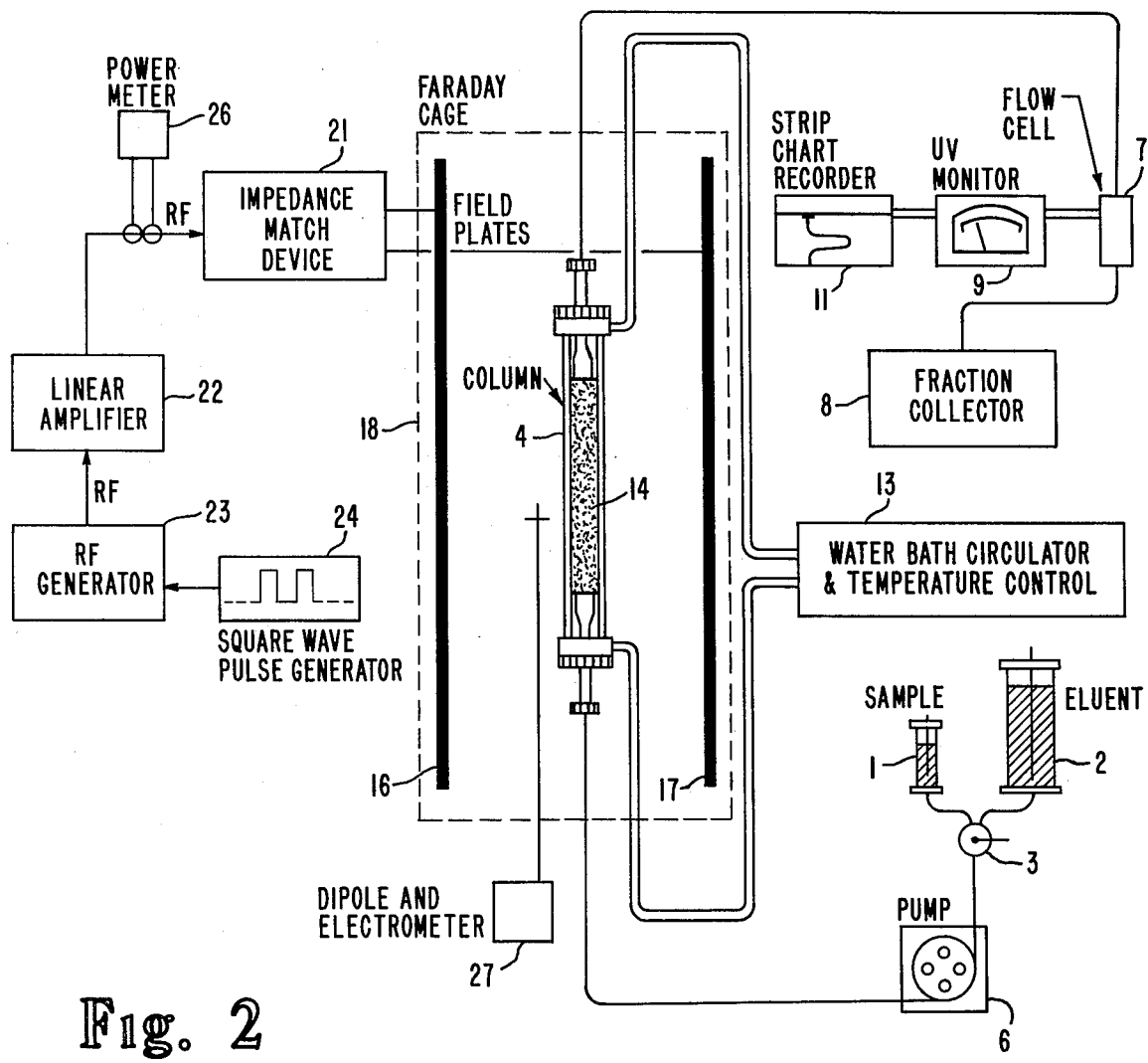
FIG. 2 is a schematic block diagram of the apparatus used to perform electric resonance chromatography (ERC).
Figure 3:
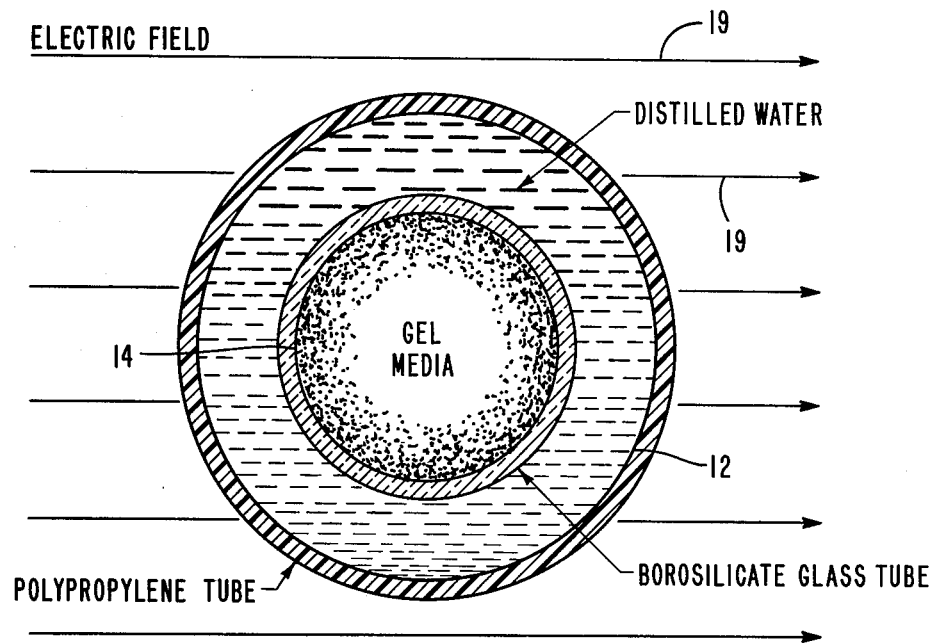
FIG. 3 is a cross-section of the chromatography column, showing the impressed electric field.

Consider the schematic block diagram of one embodying apparatus, as it appears in FIG. 2 of the drawings. The right side of the figure consists of the pieces forming a fairly conventional gel permeation type LGC structure, in this case using an ascending column orientation. The left side of the same figure depicts in conventional block diagram form the elements needed to generate and control the varying electric field. In the center of the figure the two interact to form the essential feature of the embodiment. As shown, the LGC column is centered between a set of parallel plates which create the electric field and impress it on the column and sample molecules passing through the column. A cross-section of the column itself is shown in FIG. 3, taken at a point about midway along its length.

Since the LGC apparatus consists of well known commercially available equipment, its operation need not be described with particularity. In general, though, sample material 1 and eluent 2 are selectively regulated by valve 3 and then driven through gel column 4 by pump 6. Valve 3 has three positions; a position in which both sample and eluent are off, a position in which only the sample passes, and a position in which only the eluent passes. The output from column 4 is directed through a detector, flow cell 7, and then enters fraction collector 8. UV monitor 9 responds to variations in the material passing through flow cell 7 and permanently records those signals on strip chart recorder 11. Column 4, and the materials passing through it, are maintained at a substantially constant temperature by the circulation of distilled water 12 at 25° C. through its outer jacket, clearly appearing in FIG. 3, by means of water bath circulator and temperature control 13.

More specifically as to the structure of this embodiment, sample material 1 consists of three purified globular proteins mixed in equal amounts by weight, bovine serum albumin (BSA, m.w. 69,000d), ovalbumin (OVA, m.w. 45,000d), and ribonuclease - A (R-A, m.w.

13,700d). All three were supplied by Calbiochem-Behring (San Diego, Calif.). Eluent 2 used in this embodiment is commonly known as phosphate buffered saline, with a pH of 6.95 at 25° C., formed from 0.9% W/V saline in glass distilled $H_2O$ to which is added 0.05 M phosphate buffer. Column 4 is a model K-26 manufactured by Pharmacia Fine Chemicals (Piscataway, N.J.), while reference numerals 7, 8, 9 and 11 designate pieces of automated monitor-collector equipment from Instrument Specialties Company (Lincoln, Nebr.). Gel media 14, for purposes of this particular embodiment, was Sephadex G-200 (superfine), though similar results were later obtained using Sephadex G-100 and Sephacryl G-200. All three gel media materials are trademark products manufactured by Pharmacia Fine Chemicals.

Since the control of the material admitted into pump 6 from valve 3 conformed to the manufacturer's instructions when using gel media 14 and column 4, it need only be noted that the embodying example used 1–2 mg of the mixture in sample 1 to create the response described and plotted herein. Procedurally, valve 3 is first set to fill column 4 with eluent 2. Once the column is filled, valve 3 is set to allow sample 1 flow until 1–2 mg are introduced. Thereafter, the valve is returned to its eluent flow position. Eluent flow is maintained until the column is cleared of sample material.

The electrical aspects of this invention focus on the action of the varying electric field as it interacts with the material in column 4. As is depicted in FIG. 2, the varying electric field is created by a set of near-field synthesizer electric field capacitor plates 16 and 17. Column 4 is situated substantially parallel to and midway between the capacitor plates. A faraday cage or shielded room, represented by dashed line 18, encloses the plates and column. The faraday cage is sufficiently large to prevent self-resonance at any frequency of interest. The field between plates 16 and 17 is substantially uniform, with a peak electric field intensity magnitude of 8500 V/m at the carrier frequency of 10 MHz. The carrier is further modulated at a rate of 16 Hz for the particular embodiment described herein. Inside gel media 14 the corresponding electric field intensity was calculated to be approximately 20.5 V/m. The detailed structure of the near-field synthesizer creating these electric fields is described with great particularity in the National Bureau of Standard (NBS) Technical Note 652, issued in May 1974 and entitled "Development and Construction of an Electromagnetic Near-Field Synthesizer".

The excitation for field plates 16 and 17 is coupled through impedance matching device 21; this device is also described in the NBS Technical Note. Impedance matching device 21 is a tuneable network, for adjusting the resonant frequency of the two capacitor plates, and further includes a balun transformer for impedance matching the 75 ohm coaxial input cable to the 300 ohm input impedance of the capacitor plates and preceeding tuning network.

The 10 MHz RF power entering impedance matching device 21 comes from linear amplifier 22. The RF signal controlling the amplifier is generated in RF generator 23 and modulated by signals from square wave pulse generator 24.

Power meter 26 and dipole and electrometer 27 monitor the RF drive and electric field.

In general, the interaction of the varying electric field with the gel and sample materials, as embodied, accelerates the elution rate while reducing the zone broadening effects of the elution response. The early elution aspect, as a response, is similar to that which would appear if the molecular weights of the sample were increased. The narrowing of zones in the response is a beneficial attribute of ERC, but has yet to be fully understood as to its mechanism.

The presence of the RF electric field induces changes in the sample mixture of proteins, which respond as if they experienced an increase in molecular weight and stokes radius. These apparent increases are attributable to perturbations in the shape of the sample molecules; the degree of the distortion being dependent on net dipole moment and the orientations of the dipoles within the molecular chain. As the varying electric field induces new modes of rotation and vibration in the net and individual dipoles, the effective radii of the sample molecules increases. When compared to conventional gel permeation type LGC, the apparent rise in molecular weight and strokes radius inhibits the more polarizable macromolecules from penetrating the gel matrix, leading to earlier and narrower elution responses.

Figure 4:
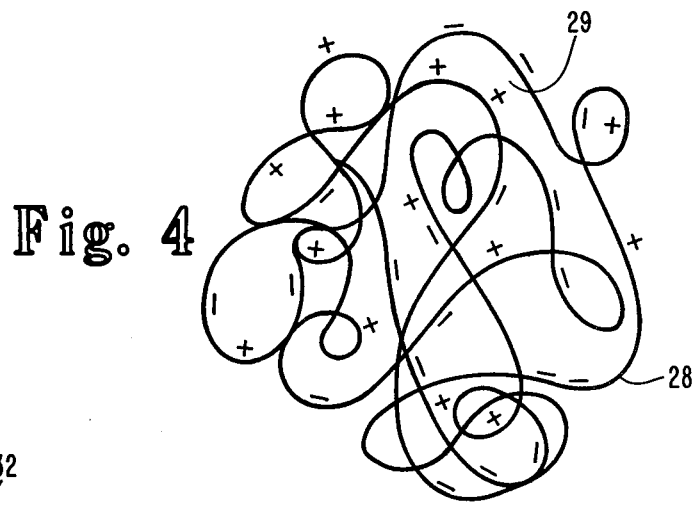
FIG. 4 schematically shows a protein chain with individual dipoles distributed on it.
Figure 5:
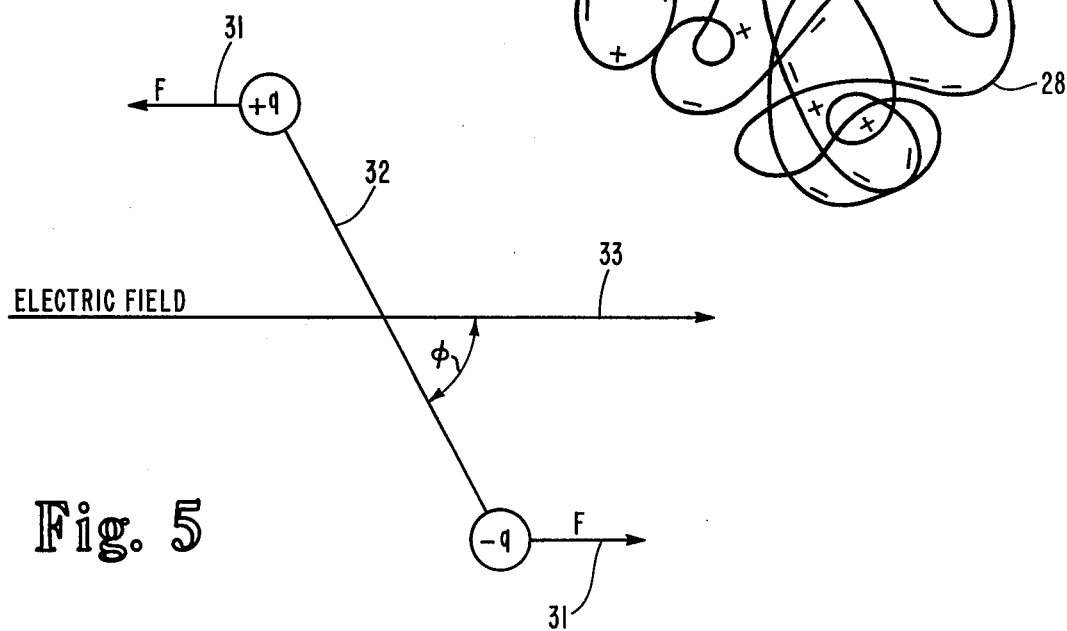
FIG. 5 is a schematic of a single dipole, or the net molecular dipole, interacting with an electric field.

Consider, in further explanation of this principle, a schematic protein molecule chain, 28, as depicted in FIG. 4. A multitude of individual dipoles 29 are dispursed along the chain at near-random orientations and locations. The application of an electric field acts on each dipole to alter its alignment. The final orientation of any single dipole is, nevertheless, still related to the redistributed alignments of all the dipoles along the chain. Since the magnitude of the electric field created aligning force 31 acting on any dipole, such as dipole 32 in FIG. 5, is influenced by both the magnitude of electric field 33 and the angle $\phi$, the complexity of the total interaction prevents direct theoretical analysis.

The sample molecules undergoing ERC may or may not have a net dipole moment. In either case, the molecules will still have multiple individual dipoles distributed along the molecular chain. When the molecules do exhibit a net dipole moment, the interaction with the electric field will respond with the effects of both the net and individual dipoles. On the other hand, the absence of a net dipole moment does not preclude interaction with the field, but rather lessens the degree of molecular distortion.

A full recognition of all the mechanisms and their degree of contribution toward altering the elution patterns during ERC is not readily discernible. To a degree, this is a result of concurrent interactions. One such interaction involves the presence of smaller molecules in the varying electric field for a longer period of time by nature of convention LGC action. The effects of the varying field are superimposed. Though recognized herein as contributing to the shape of the overall elution pattern, the effects of this interaction are well beyond the scope of the invention as disclosed and claimed.

As the varying electric field is applied to the sample molecules, their shape is distorted. Reversing the direction of the field changes the distortion. And if the field is completely removed, the molecular shape reverts to its relaxed state. In this fashion, new rotation and vibration modes enlarge the apparent molecular weight and stokes radius, and thereby, alter its elution characteristics to create unique separation patterns related to the dipole distribution of the molecule.

Another aspect of the dipole activity induced by the electric field relates to the degree of force 31 needed to overcome the rotary friction attributable to solvent visocity, and that necessary to compensate for the rotary diffusion force caused by the kinetic thermal energy of the molecules.

In both general types of influences created by the varying electric field, a relaxation time is associated with each new equilibrium position for the molecule. For the particular three proteins being considered in the embodiment, one microsecond is equivalent to infinite time for both influences. Therefore, a field varying at 10 MHz is sufficiently slow to permit complete dipole reorientation between cycle peaks.

To further elaborate on the process and apparatus concepts disclosed above, consider the specific embodiment in FIG. 2. Sample 1 is a mixture in equal proportions by weight of three purified globular proteins, BSA, OVA and R-A. The partitioning output response, in terms of absorbancy measured by UV monitor 9, verses effluent volume entering fractional collector 8, is graphically displayed in FIG. 6. Control samples of the protein mix were eluted before and after the run in which the RF electric field was imposed to verify calibration. As shown, the pre and post electric field elution curves, solid line 34, are identical. The presence of the RF electric field produced the elution profile of dashed line 36.

The elution peaks corresponding to BSA, OVA and R-A are individually designated, with their molecular weights shown in parenthesis. The enhanced elution exhibited by dashed line 36 is quite evident not only as to its earlier occurrence, but also as to depth of troughs 37 between adjacent peaks. The first mentioned characteristic corresponds to an increased elution rate, typifying an increased molecular weight or stokes radius. The second is best described in terms of its effect, this being enhanced distinction of adjacent peaks for superior purification of mixed molecules. The interesting aspect of the latter characteristic is its presence in the elution pattern without an accompanying drop in the magnitudes of the peaks.

Partitioning of mixtures, such as the three proteins described above, by permeation through a gel is characterized by a partition coefficient, $K_{av}$. Partition coefficient $K_{av}$ is defined as a relationship of volumes; i.e.

$$K_{AV} = (V_e - V_o)/(V_t - V_o),$$

where $V_e$ = elution volume for the proteins,
$V_o$ = void volume for the packed column, and
$V_t$ = total volume for the packed column.

This parameter is essentially independent of column dimensions and the compaction degree of the gel bed.

Figure 6:
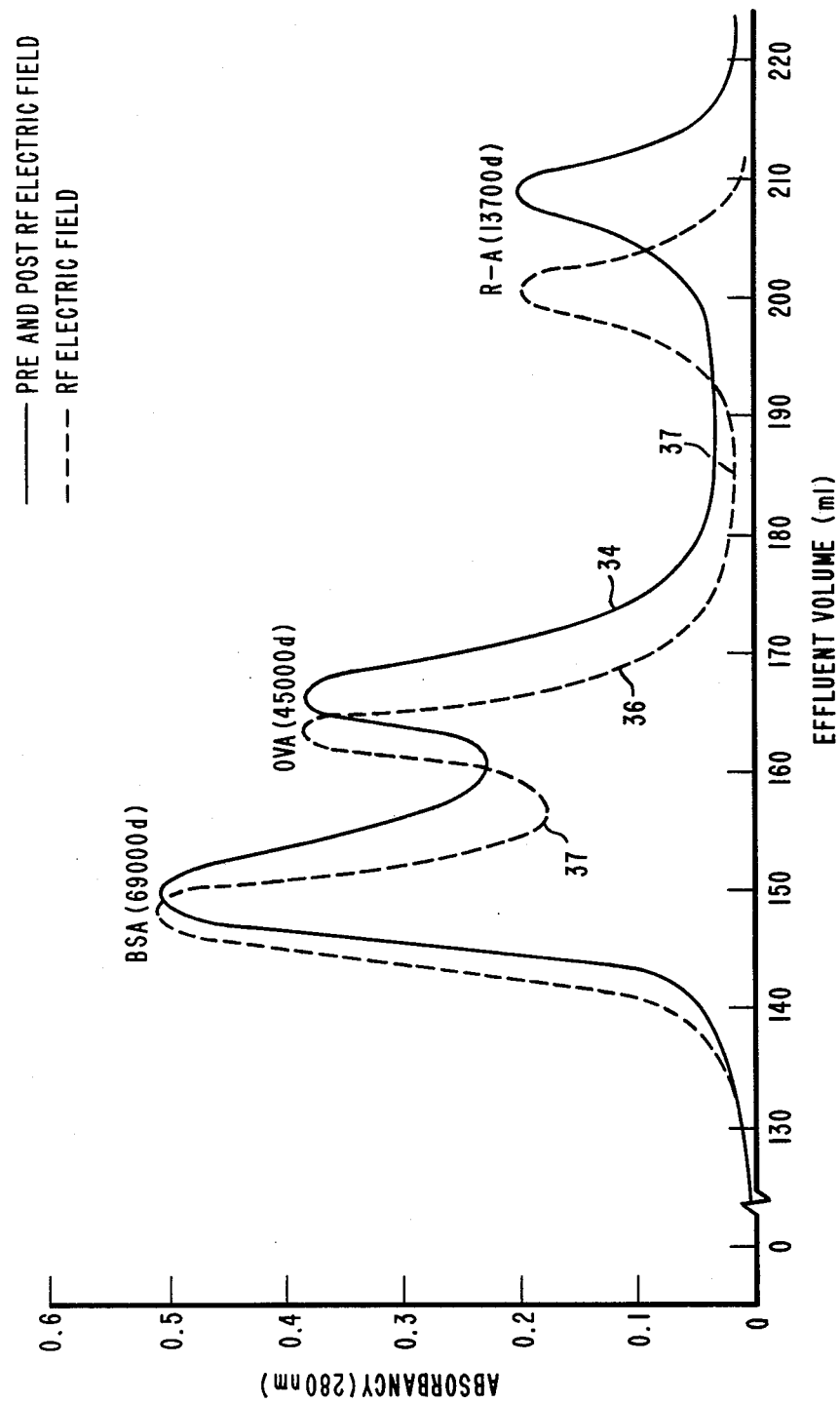
FIG. 6 contains elution plots for the embodiment, both with and without the electric field.

FIG. 7 contains a plot of $K_{av}$ verses the log of molecular weight for the elution data plotted in FIG. 6. Lines 38 and 39 join data taken under comparable operating conditions during elution. A comparison of the pre and post RF electric field values for $K_{av}$ against the values during the RF electric field indicates again that the presence of the field causes an apparent rise in molecular weight. For instance, consider the case of R-A protein having a known molecular weight of 13,700 d; the log of this magnitude being 4.14. Without the RF electric field $K_{av}$ is calculated from the elution pattern to have a value of $4.9 \times 10^{-3}$, reference point 41 of FIG. 7. With the effects of the electric field, the elution response calculates to a $K_{av}$ of $4.4 \times 10^{-3}$, appearing as reference point 42. To determine what a $K_{av}$ of $4.4 \times 10^{-3}$ represents in gel permeation type LGC, project across to point 43 on line 39. Following dotted line 44 down to the molecular weight axis of the plot, the corresponding weight is found to be 16,790 d, the antilog of 4.225. The elution response with an RF electric field present, thereby, can be said to increase the apparent molecular weight of R-A by 22.6%. Repeating this process for OVA and BSA reveals corresponding molecular weight rises of 7.6% and 0.27%, respectively.

The above-exemplified three proteins are all globular in shape. ERA would be expected by those skilled in the art to alter the elution characteristics of asymmetric, fibrous proteins to an even further degree, since large frictional and rotary diffusion forces would act to prevent rapid relaxation during field variations.

As another consideration, the invention as embodied and described in the foregoing recognized and fully contemplates other variations in the character of the electric field. One such is the absence of square wave pulse generator 22, so that the varying field, at RF or otherwise, is continuously present during elution. Preliminary experiments have shown this to be viable. In conjunction with this variant, selective tuning of the frequency or the electric field intensity to optimize the separation characteristics are similarly contemplated.

The overall scope of the invention encompasses gel beds and sample materials beyond those in the embodiment. For instance, Sephadex G-100 (fine) and Sephacryl G-200, trademark products of Pharmacia Fine Chemicals, have performed similarly. Because of their likeness to the above-name products insolubilized dextran, copolymerized acrylamide and agarose would be expected to respond substantially the same. The invention, therefore, broadly encompasses the use of all gel materials which selectively absorb or otherwise selectively interact with substances from a solution passing therethrough.

The term liquid gel chromatography (LGC) when used herein implies the art in its broadest sense. Namely, the term includes, but is not limited to, species such as affinity liquid gel chromatography, ion exchange liquid gel chromatography, and fairly conventional gel permeation forms of such chromatography. Since the essential process and apparatus features of this invention are broad, yet situated within a highly fluid art, their equivalents should not be circumscribed by the structural or material limitations of the present art.

I claim:

1. A method for enhancing the partitioning of molecules having net dipole moments or distributed dipoles within their molecular chains using liquid gel chromatography, which comprises the application of a time-varying electric field through the gel media to alter the apparent molecular size.

2. The method according to claim 1, wherein the varying electric field is applied through the gel media in a direction substantially transverse to the overall direction of molecular flow through the media.

3. The method according to claim 1, wherein the electric field varies at a frequency related to the relaxation time of the molecules being partitioned.

4. A method for inducing new vibration and rotation modes in molecules having net dipole moments or distributed dipoles within their molecular chains to alter their apparent physical and chemical properties for partitioning purposes, comprising the impression of a time-varying electric field through said molecules during partitioning.

5. The method as described in claim 4, wherein said molecules are cells or proteins and said electric field varies at a rate close to the resonant frequency of the molecules.

6. In a liquid gel chromatography apparatus having a gel media for partitioning molecules with net dipole moments or distributed dipoles within their molecular chains, an improvement, comprising a means for creating a time-varying electric field through said gel media.

7. The improvement as recited in claim 6, wherein said electric field varies at a rate close to the resonant frequency of the molecules.

8. The improvements as recited in claim 6 or 7, wherein the direction of the electric field is substantially transverse to the direction of general molecular flow through the gel media.

* * * * *

UNITED STATES PATENT AND TRADEMARK OFFICE
CERTIFICATE OF CORRECTION

PATENT NO. : 4,238,327
DATED : December 9, 1980
INVENTOR(S) : Robert P. Liburdy

It is certified that error appears in the above-identified patent and that said Letters Patent are hereby corrected as shown below:

Col 6, line 1, change "antilong" to --- antilog ---.

Signed and Sealed this

Fourteenth Day of April 1981

[SEAL]

Attest:

RENE D. TEGTMEYER

Attesting Officer     Acting Commissioner of Patents and Trademarks